United States Patent
Chen et al.

(10) Patent No.: US 12,102,690 B2
(45) Date of Patent: Oct. 1, 2024

(54) PREPARATION METHOD AND APPLICATION OF BIOMIMETIC NANO-PROTECTANT FOR DETOXIFYING DOX-INDUCED CARDIAC AND SYSTEMIC TOXICITY

(71) Applicant: The Second Affiliated Hospital of Wenzhou Medical University, Wenzhou (CN)

(72) Inventors: Yijie Chen, Wenzhou (CN); Mengchun Chen, Wenzhou (CN); Weiliang Xia, Wenzhou (CN); Deli Zhuge, Wenzhou (CN); Haiyan Zhu, Wenzhou (CN); Yingzheng Zhao, Wenzhou (CN); Qi Jiang, Wenzhou (CN)

(73) Assignee: THE SECOND AFFILIATED HOSPITAL OF WENZHOU MEDICAL UNIVERSITY, Wenzhou (CN)

( * ) Notice: Subject to any disclaimer, the term of this patent is extended or adjusted under 35 U.S.C. 154(b) by 0 days.

(21) Appl. No.: 18/287,463

(22) PCT Filed: Jun. 27, 2022

(86) PCT No.: PCT/CN2022/101401
§ 371 (c)(1),
(2) Date: Oct. 19, 2023

(87) PCT Pub. No.: WO2023/274105
PCT Pub. Date: Jan. 5, 2023

(65) Prior Publication Data
US 2024/0207436 A1    Jun. 27, 2024

(30) Foreign Application Priority Data
Jul. 1, 2021   (CN) .......................... 202110746762.6

(51) Int. Cl.
A61K 47/69 (2017.01)
A61K 47/64 (2017.01)
A61P 39/02 (2006.01)

(52) U.S. Cl.
CPC ........ *A61K 47/6901* (2017.08); *A61K 47/646* (2017.08); *A61K 47/6935* (2017.08); *A61P 39/02* (2018.01)

(58) Field of Classification Search
CPC .............. A61K 47/6901; A61K 47/646; A61K 47/6935; A61P 39/02
See application file for complete search history.

(56) References Cited

FOREIGN PATENT DOCUMENTS

| CN | 102764442 A | 11/2012 |
|----|-------------|---------|
| CN | 107815470 A | 3/2018 |
| CN | 110755613 A | 2/2020 |
| CN | 111494605 A | 8/2020 |
| CN | 113546056 A | 10/2021 |
| CN | 113577039 A | 11/2021 |
| CN | 113599531 A | 11/2021 |
| WO | 9418947 A1  | 9/1994  |

OTHER PUBLICATIONS

X. Qiao, et al. Uncoupling DNA damage from chromatin damage to detoxify doxorubicin, PNAS 117 (26), Jun. 30, 2020, 15182-15192 (Year: 2020).*

Qi Jiang, et al. "Doxorubicin Detoxification in Healthy Organs Improves Tolerability to High Drug Doses for Enhanced Antitumor Therapy," ACS Nano 2023, 17, 8, 7705-7720. (Year: 2023).*

Xueyan Liu, et al., In vitro and in vivo evaluation of liposomes modified with polypeptides and red cell membrane as a novel drug delivery system for myocardium targeting, Drug Delivery, 2020, pp. 599-606, vol. 27, No. 1.

Ye Jie-Sheng, et al., Preliminary Studies on Protamine-pDNA Complex Loaded Solid Lipid Nanoparticles, Chin Pharm J, 2007, pp. 1644-1648, vol. 42, No. 21.

Xin Wang, Research on PCM and TAT dual-modified liposome myocardial targeted delivery system, 2017, pp. 1-73.

* cited by examiner

*Primary Examiner* — Michael P Cohen
(74) *Attorney, Agent, or Firm* — Bayramoglu Law Offices LLC

(57) ABSTRACT

A preparation method and application of a biomimetic nano-protectant for detoxifying doxorubicin (DOX)-induced cardiac and systemic toxicity are provided. The preparation method comprises the following steps: obtaining and mixing DNA and protamine (Pro) to prepare DNA&Pro nanoparticles; reacting heterofunctional polyethylene glycol DSPE-PEG2000-MAL with PCM/KALA to prepare DSPE-PEG2000-PCM/KALA; inserting DSPE-PEG2000-PCM/KALA into a surface of Red Blood Cell Membrane (RBCM) to prepare PCM/KALA-RBCM; and mixing the RBCM-PCM/KALA with the DNA&Pro nanoparticles to prepare a biomimetic nano-protectant DNA&Pro@RBCM-PCM/KALA. The biomimetic nano-protectant prepared is applied to detoxification of DOX.

9 Claims, 17 Drawing Sheets
Specification includes a Sequence Listing.

RBCM  DNA  OVERLAY

PREPARATION METHOD AND APPLICATION OF BIOMIMETIC NANO-PROTECTANT FOR DETOXIFYING DOX-INDUCED CARDIAC AND SYSTEMIC TOXICITY

CROSS REFERENCE TO THE RELATED APPLICATIONS

This application is the national phase entry of International Application No. PCT/CN2022/101401, filed on Jun. 27, 2022, which is based upon and claims priority to Chinese Patent Application No. 202110746762.6, filed on Jul. 1, 2021, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBOY057_Sequence Listing-20231109-1835-LS_ST25.txt, created on Nov. 9, 2023, and is 2,687 bytes in size.

TECHNICAL FIELD

The present invention relates to the technical field of biomedicines, in particular to a preparation method and application of a biomimetic nano-protectant for detoxifying doxorubicin (DOX)-induced cardiac and systemic toxicity.

BACKGROUND OF THE INVENTION

DOX, as a classic chemotherapeutic drug, is widely applied to the treatment of different types of cancer. Although DOX shows a good therapeutic effect on cancer, toxic side effects (including cardiotoxicity, hepatotoxicity, and gastrointestinal reaction) of DOX profoundly limit its further clinical applications. It is well-known that a main mechanism of DOX killing cancer cells is to bind to double-stranded DNA in cancer cells to inhibit DNA replication within cell nucleus and induce cell apoptosis. In addition, DOX can be specifically inserted into GC base pairs of DNA double strands. According to the characteristic, it has been studied to insert DOX into plasmids and other double-stranded nucleic acids to realize the co-delivery of nucleic acids and DOX.

The prior invention patent application No. CN202010284531.3 discloses a medical use of CREG protein for preventing or treating DOX-induced myocardial damage. It is known from the description of the patent application text that the myocardium and/or liver may be damaged even after timely treatment of the damaged myocardium in the invention, which still brings a great burden to patients.

BRIEF SUMMARY OF THE INVENTION

In view of shortcomings in the prior art, an objective of the invention is to provide a preparation method and application of a biomimetic nano-protectant for detoxifying DOX-induced cardiac and systemic toxicity, which can solve a problem of damage to myocardium and/or liver during treatment of cancer in the prior art and reduce physical burden of patients.

To achieve the objective, the invention provides the following technical solution: a preparation method of a biomimetic nano-protectant for detoxifying DOX-induced cardiac and systemic toxicity, including the following steps:
  obtaining and mixing DNA and protamine (Pro) to prepare DNA&Pro nanoparticles;
  reacting 1,2-distearoyl-sn-glycero-3-phosphoethanolamine-N-[maleimide(polyethylene glycol)-2000] (DSPE-PEG2000-MAL) with PCM/KALA to prepare DSPE-PEG2000-PCM/KALA;
  inserting DSPE-PEG2000-PCM/KALA into a surface of Red Blood Cell Membrane (RBCM) to prepare PCM/KALA-RBCM; and
  mixing the RBCM-PCM/KALA with the DNA&Pro nanoparticles to prepare a biomimetic nano-protectant DNA&Pro@RBCM-PCM/KALA.

Preferably, the biomimetic nano-protectant DNA&Pro@RBCM-PCM/KALA is prepared by an Extrusion method after the RBCM-PCM/KALA is mixed with the DNA&Pro nanoparticles.

Preferably, a ratio of DNA:protamine:RBCM:DSPE-PEG2000-MAL:PCM/KALA is 6:5:150:3.75:7.5 (w/w).

Preferably, the adopted DNA takes green fluorescent protein plasmids as a DNA template, with a size of 630 bp and a GC content of 65%.

Preferably, DNA and Pro are mixed to form DNA&Pro nanoparticles by ultrasonic treatment for 20 s.

Preferably, a nitrogen-phosphorus ratio of a mixture of DNA and Pro satisfies that N/P=2.

Preferably, a ratio of DSPE-PEG2000-MAL to PCM/KALA is 1:2 (mol/mol); and both DSPE-PEG2000-MAL and PCM/KALA are dissolved in ultrapure water, and incubated at 37° C. for 30-60 min to synthesize DSPE-PEG2000-PCM/KALA.

Preferably, DSPE-PEG2000-PCM/KALA and RBCM (based on membrane protein mass) are mixed at a mass ratio of 1:20 (w/w), and incubated at 37° C. for 30-60 min to prepare RBCM-PCM/KALA.

Preferably, DNA&Pro@RBCM-PCM/KALA is prepared by the Extrusion method, with a pore size of 400 nm.

The invention has beneficial effects that
1. PCM/KALA has excellent selectivity, and can be enriched to normal organs such as heart and liver instead of tumor tissues;
2. A protective barrier is constructed with the nanoparticles composed of DNA and Pro, to prevent DOX from damaging myocardium and/or liver cells and hurting human body;
3. A Red Blood Cell Membrane (RBCM) can bypass an immune system, ensuring construction efficiency and action effect of the barrier;
4. The connection between PCM/KALA and RBCM can wrap the nanoparticles composed of DNA and Pro, so that the nanoparticles for constructing the barrier can be rapidly delivered to the normal organs such as heart and liver instead of tumor tissues;
5. PCM/KALA can rapidly mediate the phagocytosis of nanoparticles by cells, to effectively improve the construction efficiency of the protective barrier;
6. The protectant escapes from lysosomes and is dispersed in cytoplasm after being phagocytized by normal cells such as myocardial cells, to effectively prevent DOX from entering the cell nucleus and preventing or alleviating cell apoptosis; and
7. The protectant never or rarely enters the tumor tissues, so that DOX can achieve an optimal tumor inhibition effect.

DETAILED DESCRIPTION OF THE INVENTION

The invention will be further described in detail with reference to embodiments given in the accompanying drawings.

Referring to FIGS. 1-6, 7A-7C, 8-14, 15A-15D, 16-19, and 20A-20C,

Example 1

Preparation of RBCM

Figure 1:
FIG. 1 is a schematic diagram of collecting a purified RBCM.

Red blood cells were obtained from C57BL/6 rats (B6 rats) by the following process: the whole blood of B6 rats was collected, and then centrifuged at 3000-5000 rpm for 15 min to remove white blood cells, blood platelets and serum to obtain red blood cells. 250 µL of red blood cells were added into 950 µL of ultrapure water and then subjected to ice bath for 30-60 min; 20×PBS was added to adjust the osmotic pressure to 1×, and was centrifuged at 14000 rpm for 10 min after being well mixed; then, supernatant was discarded; 950 µL of ultrapure water was added for resuspension, and ice bath, adjustment of the osmotic pressure and centrifugation were then carried out again, and the same process was cycled until hemoglobin was absent in the supernatant; and precipitates were collected (FIG. 1). The collected precipitates were the RBCM. The concentration of membrane protein in RBCM was determined by a BCA method.

Example 2

Preparation of DNA Rich in 65% GC Base Pairs

Figure 2:
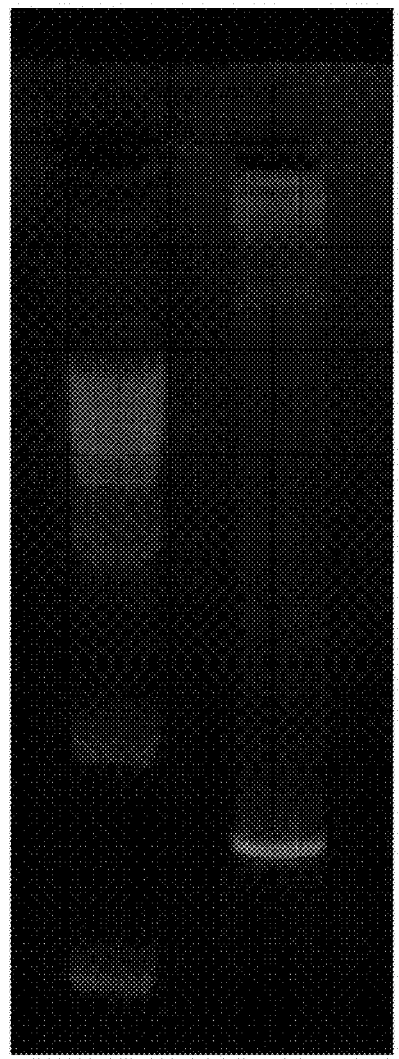
FIG. 2 is a schematic diagram of verifying the size of a target DNA fragment.
Figure 3:
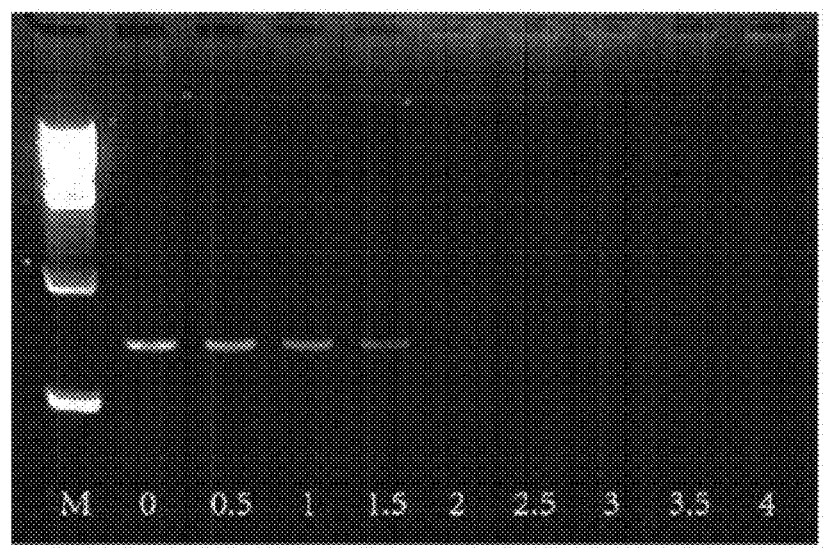
FIG. 3 is a schematic diagram of Pro's ability to compress DNA at different N/P ratios.

Taking green fluorescent protein plasmids as DNA templates, a forward primer CGGCCACAAGTTCGTGAT, as shown in SEQ ID NO: 1, and a reverse primer AATCCAGAGGTTGATTGTTCCA, as shown in SEQ ID NO: 2 were designed to obtain a DNA fragment with a size of 630 bp and a GC content of about 65%, having a sequence of CGGCCACAAGTTCGTGATCACCGGCGAGGG-CATCGGCTACCCCTTCAAGGGCAAGCA GGCCAT-CAACCTGTGCGTGGTG-GAGGGCGGCCCCTTGCCCTTCGCCGAGGACATCTT GTCCGCCGCCTTCATGTACGGCAACCGCGTGTT-CACCGAGTACCCCCAGGACATCGT CGACTACTT-CAAGAACTCCTGCCCCGCCGGCTA-CACCTGGGACCGCTCCTTCCTGTTC GAGGACGGCGCCGTGTGCATCTGCAACGCCGA-CATCACCGTGAGCGTGGAGGAGAA CTGCATGTAC-CACGAGTCCAAGTTCTACGGCGT-GAACTTCCCCGCCGACGGCCCCGT GATGAAGAAGATGACCGACAACTGG-GAGCCCTCCTGCGAGAAGATCATCCCCGTGCC CAAGCAGGGCATCTTGAAGGGCGACGTGAG-CATGTACCTGCTGCTGAAGGACGGTG GCCGCTTGCGCTGCCAGTTCGACACCGTGTA-CAAGGCCAAGTCCGTGCCCCGCAAGA TGCCCGACTGGCACTT-CATCCAGCACAAGCTGACCCGCGAGGACCGCA-GCGACGCC AAGAACCAGAAGTGGCACCTGACCGAGCACGC-CATCGCCTCCGGCTCCGCCCTTGCCC TGAACGCGTCTGGAACAATCAACCTCTGGATT, as shown in SEQ ID NO: 3. Subsequently, the plasmid DNA was amplified by a PCR instrument; a target DNA fragment was purified and isolated; and the DNA concentration was determined by Nanodrop. The size of the DNA fragment was verified by agarose gel (FIG. 2). In FIG. 2, a left band is Marker and a right band is the target DNA fragment, with the size of about 630 bp, which is in line with the expected design.

Example 3

Ratio Screening of DNA&Pro Nanoparticles Formed by Self-assembly of DNA and Pro

Figure 4:
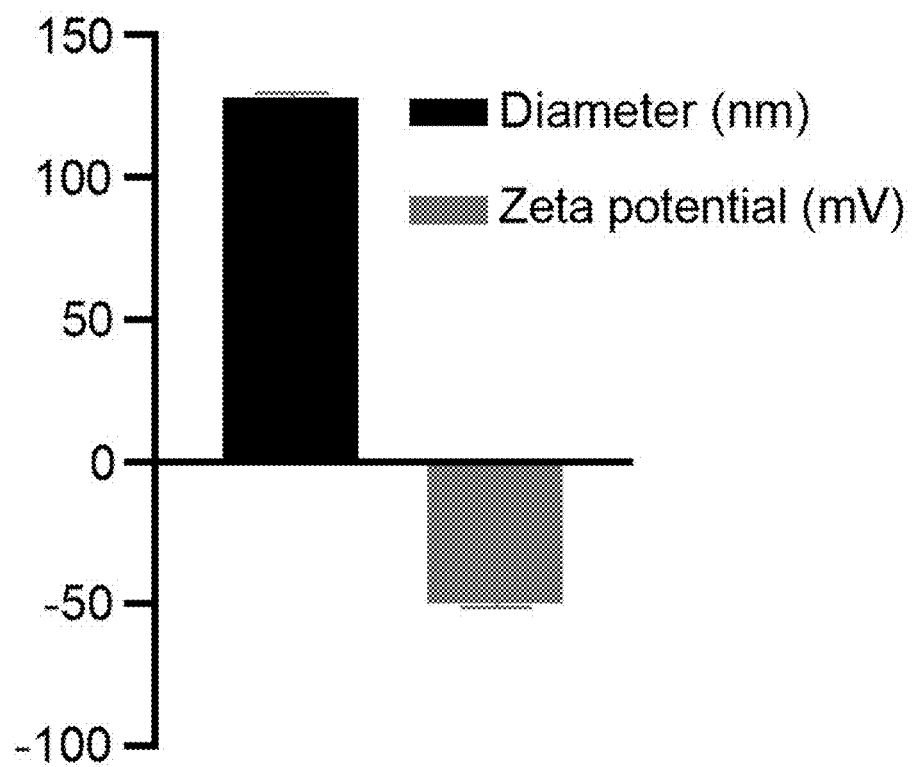
FIG. 4 is a schematic diagram of particle size and potential of DNA&Pro nanoparticles.
Figure 5:
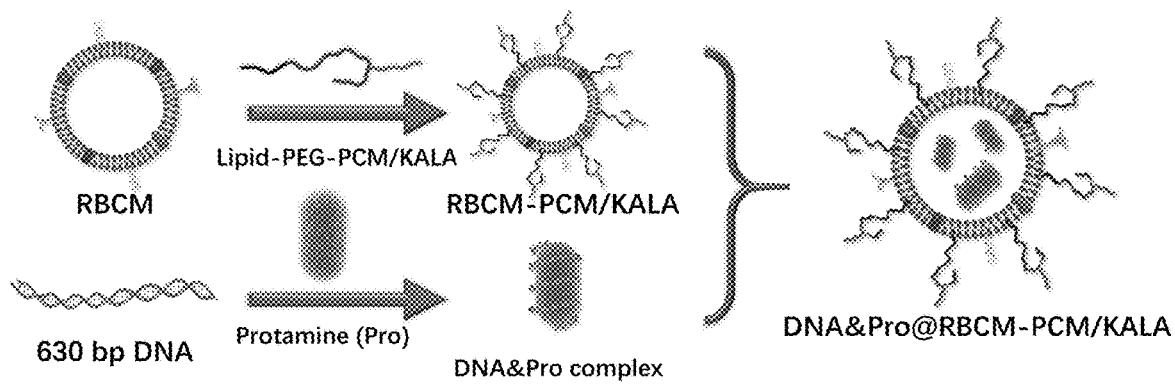
FIG. 5 is a schematic diagram of construction process of a biomimetic nano-protectant DNA&Pro@RBCM-PCM/KALA.

DNA and Pro were mixed at different nitrogen-phosphorus ratios (N/P=0, 0.5, 1, 1.5, 2, 2.5, 3, mol/mol), and ultrasonically treated for 20 s to form DNA&Pro nanoparticles for later use. Whether Pro completely compressed and wrapped DNA (FIG. 3) was detected by an agarose gel electrophoresis method. The results show that when N/P is 2, Pro can completely compress DNA into nanoparticles, so that DNA fragments cannot be in a free state and can be displaced under the action of current. Subsequently, the hydraulic size and surface potential of DNA&Pro nanoparticles were measured by a particle size potentiometer (FIG. 4). The results show that the particle size and the potential of the DNA&Pro nanoparticles are 128 nm and −50 mV, respectively.

Example 4

Construction of RBCM-PCM/KALA Biomimetic Nanoparticles

Firstly, DSPE-PEG2000-PCM and DSPE-PEG2000-PCM/KALA were prepared. DSPE-PEG2000-MAL, PCM/KALA and PCM were accurately weighed respectively, and dissolved in ultrapure water. Then, the DSPE-PEG2000-MAL and the PCM/KALA were mixed according to a ratio of DSPE-PEG2000-MAL to PCM/KALA being 1:2 (mol/mol) and the DSPE-PEG2000-Mal and the PCM were mixed according to a ratio of DSPE-PEG2000-Mal to PCM being 1:2 (mol/mol), and the mixtures were then incubated at 37° C. for 30-60 min to synthesize DSPE-PEG2000-PCM/KALA and DSPE-PEG2000-PCM respectively. Secondly, DSPE-PEG2000-PCM/KALA or DSPE-PEG2000-PCM was mixed with RBCM respectively according to a mass ratio of DSPE-PEG2000-MAL to RBCM (based on membrane protein mass) being 1:20 (w/w) to obtain a mixture; and the mixture was incubated at 37° C. for 30-60 min. After the reaction was completed, the above reactants were placed in a centrifuge and centrifuged at 14000 rpm for 10 min, to remove excess DSPE-PEG2000-PCM/KALA or DSPE-PEG2000-PCM, thereby obtaining RBCM-PCM/KALA and RBCM-PCM.

Example 5

Figure 6:
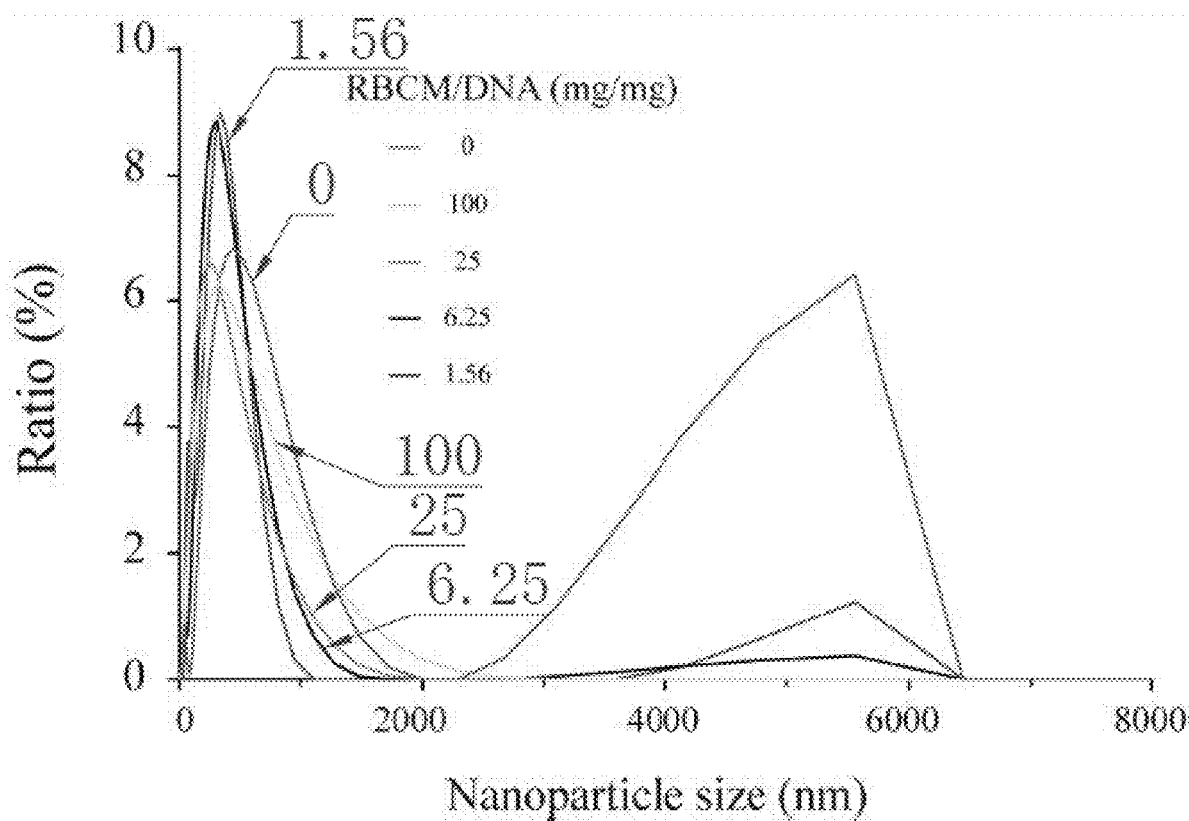
FIG. 6 is a schematic diagram of ratio screening of RBCM-PAM/KALA completely wrapping the DNA&Pro nanoparticles.
Figures 7A, 7B, 7C:
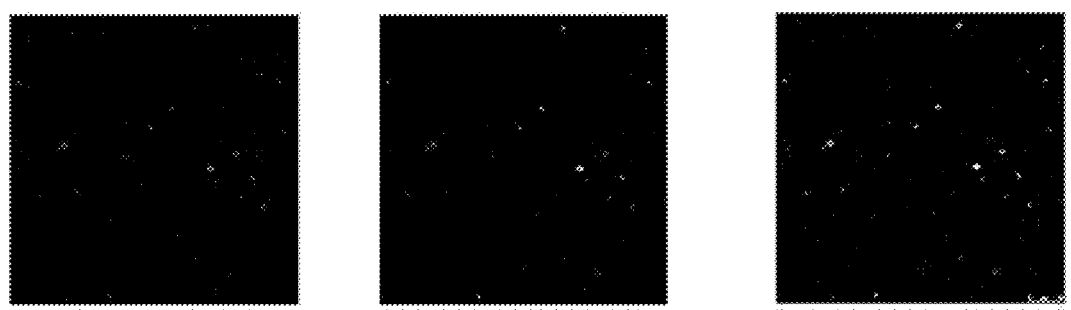
FIGS. 7A-7C show a schematic diagram of colocalization of RBCM and DNA&Pro nanoparticles studied by CLSM imaging technology.
Figure 8:
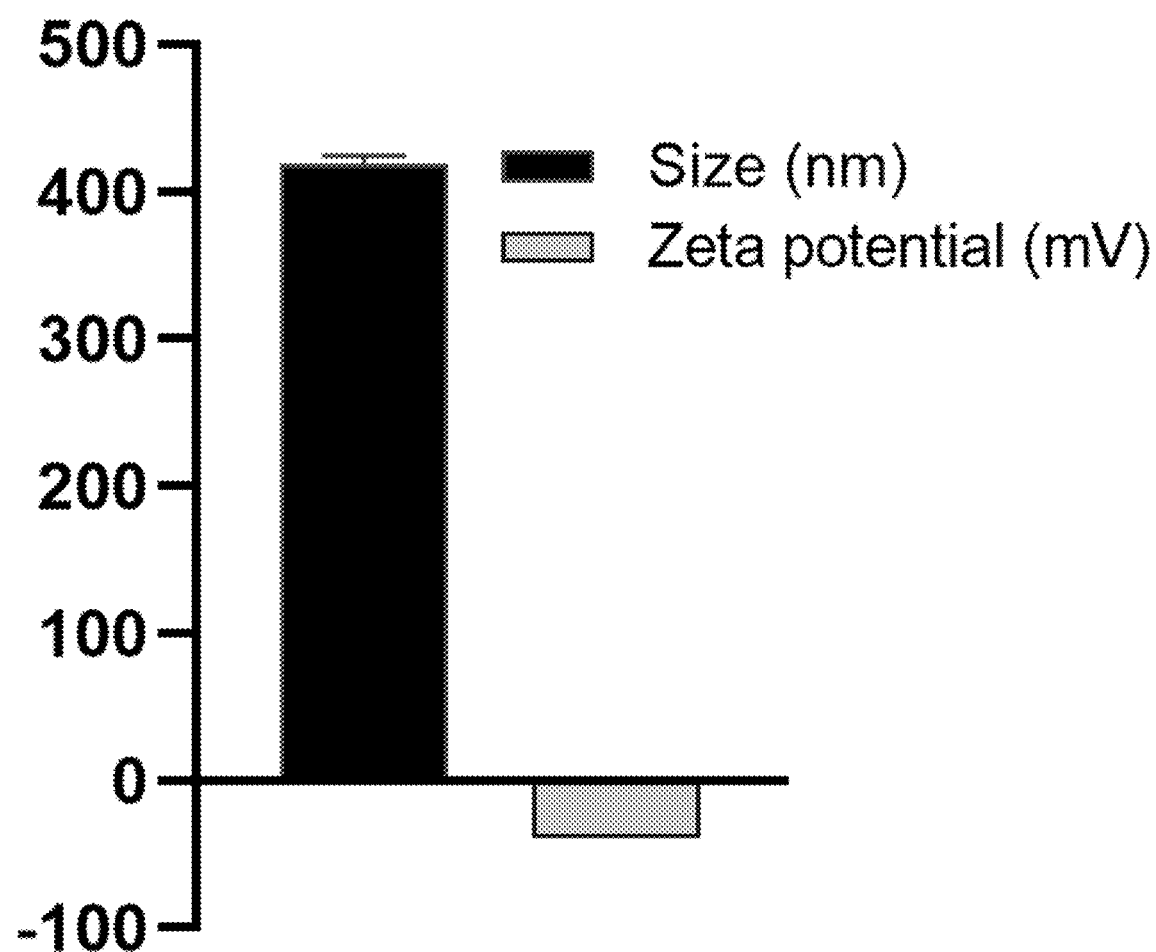
FIG. 8 is a schematic diagram of particle size and surface potential of the biomimetic nano-protectant DNA&Pro@RBCM-PCM/KALA.

Construction and Ratio Screening of Biomimetic Nano-protectant DNA&Pro@RBCM-PCM/KALA Construction process of biomimetic nano-protectant DNA&Pro@RBCM-PCM/KALA (see FIG. 5) and screening of RBCM-PCM/KALA and DNA&Pro nanoparticles in appropriate ratio were provided. Firstly, a target DNA fragment (denoted as Bio-DNA) containing biotin label was synthesized with biotinylated forward primer biotin-CGGC-CACAAGTTCGTGAT and reverse primer AATCCAGAGGTTGATTGTTCCA-biotin; and then, Bio-DNA&Pro nanoparticles were constructed according to the ratio of N/P=2 (mol/mol) for later use. The prepared RBCM-PCM/KALA was mixed with the Bio-DNA&Pro nanoparticles according to different mass ratios of RBCM membrane protein to DNA (0, 100:1, 25:1, 6.25:1, 1.56:1); and then the biomimetic nano-protectant DNA&Pro@RBCM-PCM/KALA was obtained by an Extrusion method (400 nm in aperture). Subsequently, a certain amount of streptavidin was added; and then the particle size change of nanoparticles was detected by a particle size potentiometer (FIG. 6). The results show that when the mass ratio of RBCM membrane protein to DNA is greater than 6.25:1, RBCM-PCM/KALA can completely wrap the Bio-DNA/Pro nanoparticles; and when the mass ratio of RBCM membrane protein to DNA is less than 6.25:1, a part of Bio-DNA&Pro nanoparticles will be in a free state, so the part of Bio-DNA&Pro nanoparticles can be combined with the added streptavidin to agglomerate and subject to micron-sized particle size distribution. To further confirm that RBCM-PCM/KALA completely wrapped the Bio-DNA&Pro nanoparticles, the mass ratio of RBCM-PCM/KALA was determined to be 25:1 (w/w); meanwhile, RBCM-PCM/KALA was labeled with DiD dye, and an FAM primer was used for preparing FAM-DNA; and finally, a double-labeled biomimetic nano-protectant DNA&Pro@RBCM-PCM/KALA with DiD label on RBCM and FAM label on DNA was prepared. Then, the co-location of RBCM-PCM/KALA (DiD) and DNA&Pro nanoparticles (FAM) was observed by a CLSM imaging technology (FIGS. 7A-7C). The results show that a DiD red signal representing RBCM-PCM/KALA is overlapped with an FAM green signal representing DNA, which further indicates that when the mass ratio of RBCM to DNA is 25:1, RBCM-PCM/KALA has completely wrapped the DNA&Pro nanoparticles to form the biomimetic nano-protectant DNA&Pro@RBCM-PCM/KALA. The mass ratio of RBCM membrane protein to DNA is 25:1, the mass ratio of various components of the biomimetic nano-protectant satisfies that DNA:Pro:RBCM:PCM/KALA=6:5:150:7.5 (w/w). Meanwhile, the hydraulic size and the surface potential of the constructed biomimetic nano-protectant DNA&Pro@RBCM-PCM/KALA are determined to be 400 nm and −39.4 mV, respectively (FIG. 8).

Example 6

Targeting Effect of Biomimetic Nano-Protectant DNA&Pro@RBCM-PCM/KALA on Myocardial Cells DiD fluorescent dye was respectively mixed with RBCM or RBCM-PCM or RBCM-PCM/KALA according to a mass ratio of DiD to RBCM (based on membrane protein mass) being 6:1000 (w/w) to obtain a mixture; and the mixture was incubated at 37° C. for 30 min. Subsequently, the mixture was centrifuged at 14000 rpm for 10 min to remove supernatant, and then washed with PBS for 3 times to ensure that the free DiD dye was completely removed. Meanwhile, DNA&Pro nanoparticles were synthesized for later use. Finally, the DNA&Pro nanoparticles were wrapped with RBCM or RBCM-PCM or RBCM-PCM/KALA labeled by DiD fluorescent dye according to a ratio of RBCM to DNA being 25:1 (w/w), to construct DNA&Pro@RBCM, DNA&Pro@RBCM-PCM and DNA&Pro@RBCM-PCM/KALA, respectively.

Figure 9:
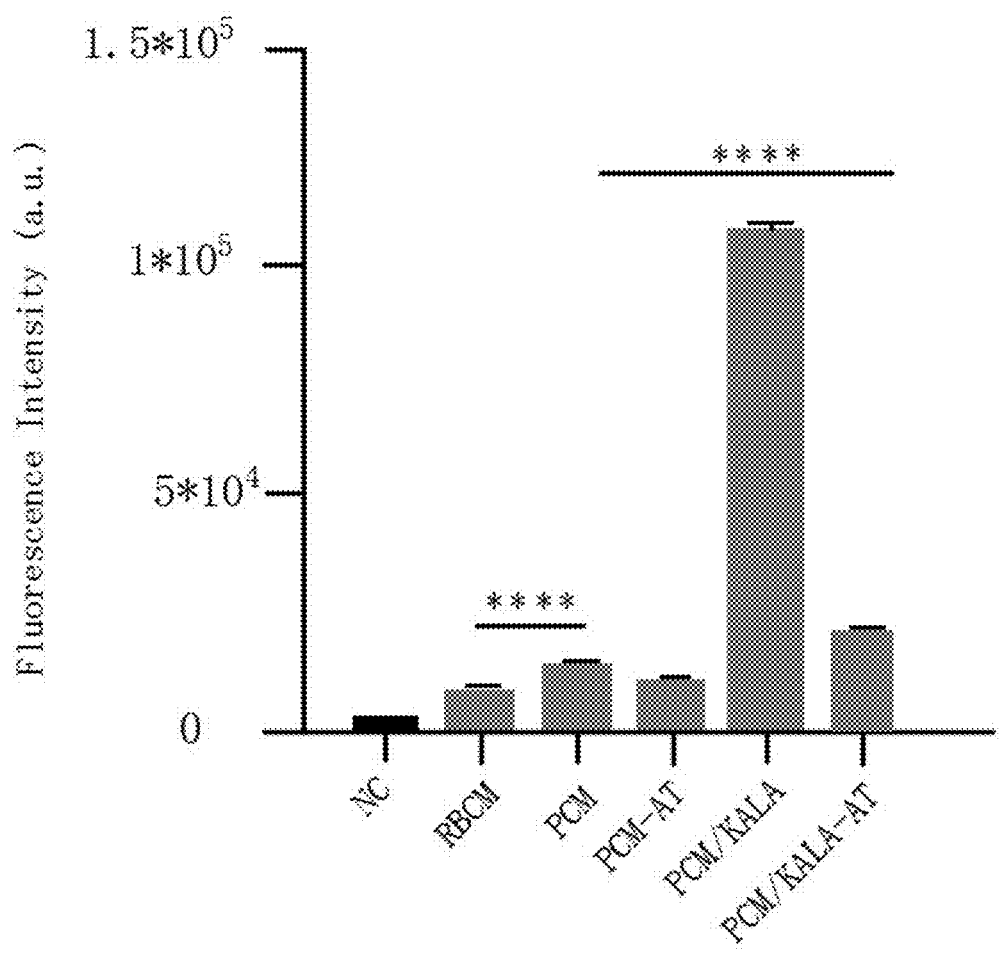
FIG. 9 is a schematic diagram of targeting effect of DNA&Pro@RBCM-PCM/KALA on myocardial cells.
Figure 10:
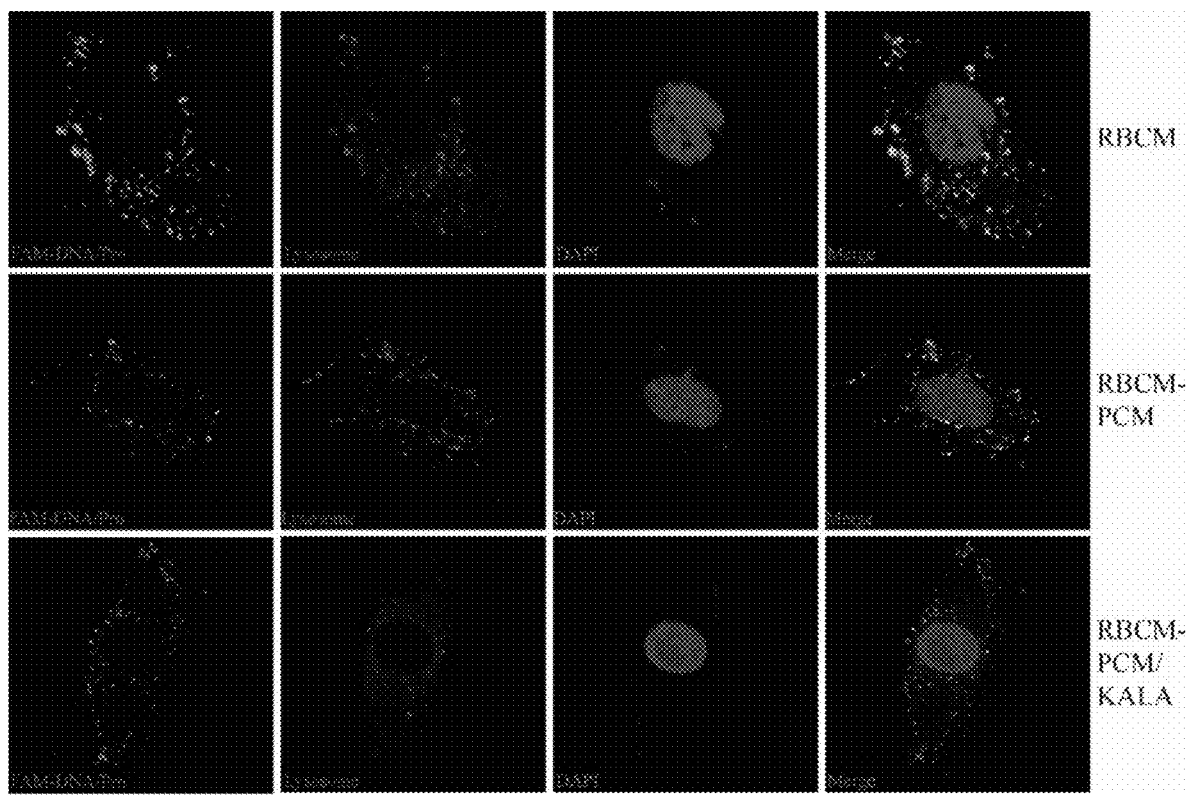
FIG. 10 is a schematic diagram of lysosomal escape ability of DNA&Pro@RBCM-PCM/KALA.
Figure 11:
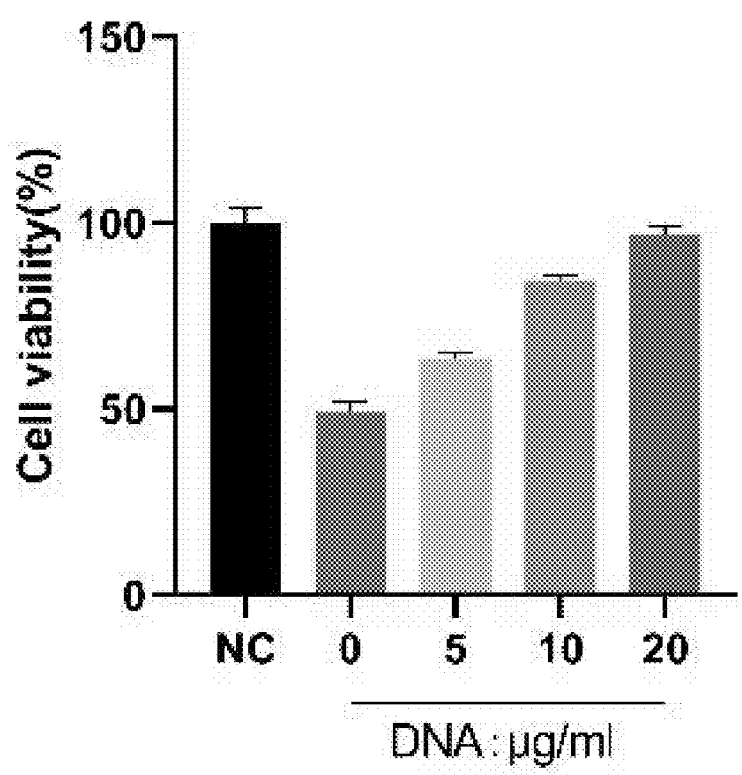
FIG. 11 is a schematic diagram of different doses of biomimetic nano-protectant DNA&Pro@RBCM-PCM/KALA protecting myocardial cells in a concentration-dependent manner.
Figure 12:
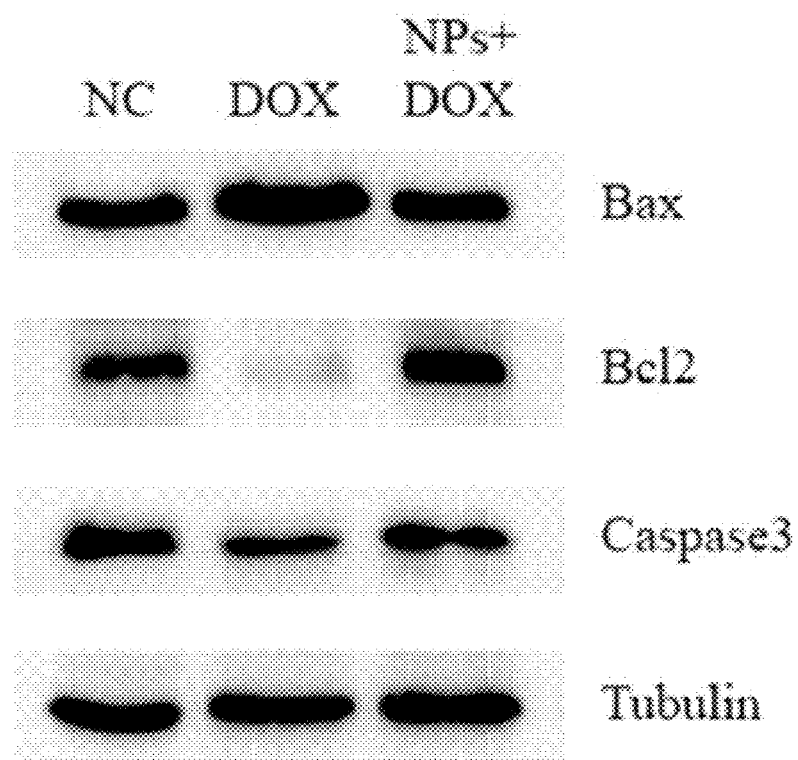
FIG. 12 is a schematic diagram of the biomimetic nano-protectant DNA&Pro@RBCM-PCM/KALA against myocardial cell apoptosis.
Figure 13:
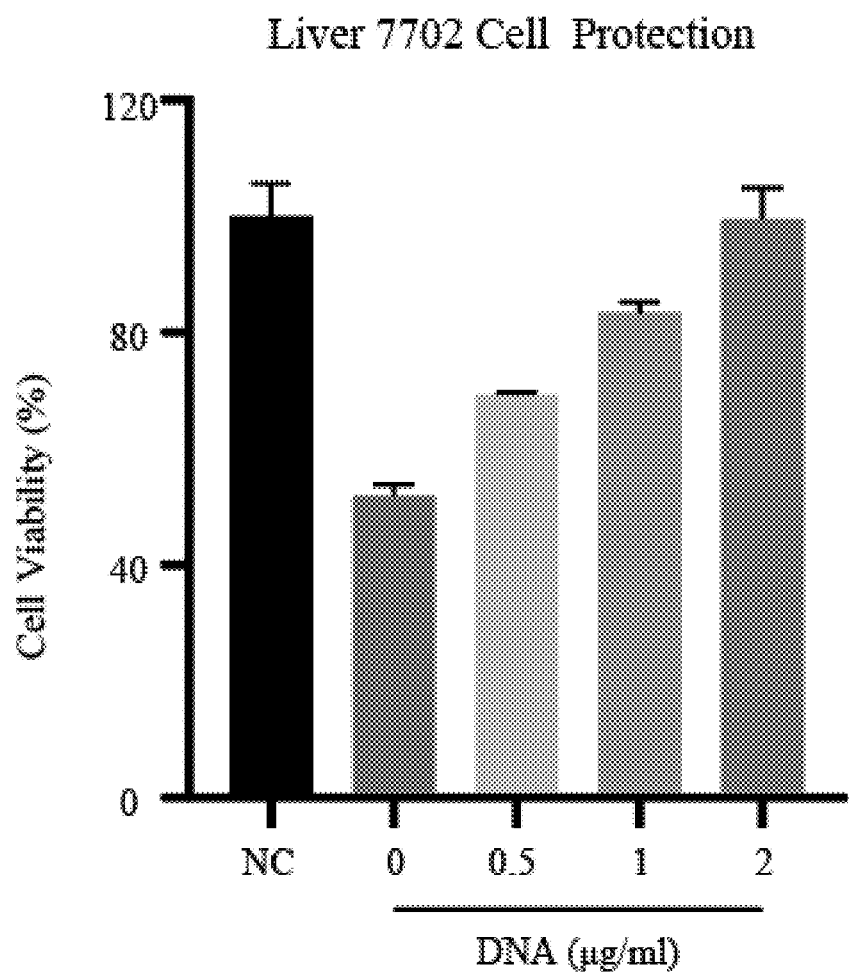
FIG. 13 is a schematic diagram of different doses of biomimetic nano-protectant DNA&Pro@RBCM-PCM/KALA protecting liver cells in a concentration-dependent manner.
Figure 14:
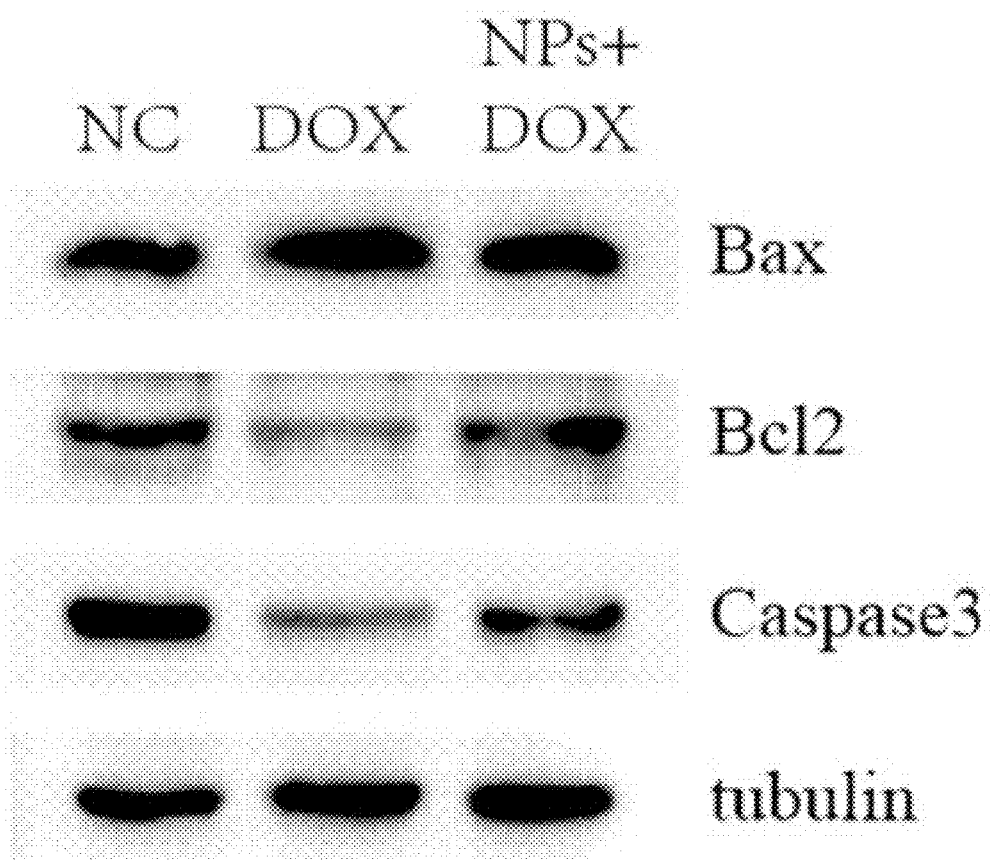
FIG. 14 is a schematic diagram of the biomimetic nano-protectant DNA&Pro@RBCM-PCM/KALA against liver cell apoptosis.

Experimental groups include: Negative Control group (NC group, treatment-free group); RBCM group (only DiD-labeled DNA&Pro@RBCM was added); 3. PCM group (only DiD-labeled DNA&Pro@RBCM-PCM was added); 4. PCM antagonistic group (free PCM was used for pretreatment for 4 h; and then DiD labeled DNA&Pro@RBCM-PCM was added); 5. PCM/KALA group (only DiD labeled DNA&Pro@RBCM-PCM/KALA was added); 6. PCM/KALA antagonistic group (free PCM/KALA was used for pretreatment for 4 h; and then DiD labeled DNA&Pro@RBCM-PCM/KALA was added). General experimental process: H9C2 cells (rat-derived myocardial cells) were cultured in 6-well plates, and added into the above different experimental groups respectively after the confluence rate reached 80%; and a uniform concentration of RBCM membrane protein in each group was 100 μg/mL. After 2 h, the supernatant was removed; and then, the cells were washed with PBS for 3 times. Subsequently, the cells were digested by trypsin into single cell suspension; and then, the intensity of a DiD fluorescence signal in the cells was detected by a flow cytometry (FCM). Statistics of experimental results of the FCM are shown in FIG. 9. The results show that targeting efficiencies of myocardial cells in the PCM group and the PCM/KALA group are about twice and 10 times higher than that in the RBCM group alone. In the PCM group, PCM only improves the affinity between particles and H9C2 cells, but cannot rapidly mediate the phagocytosis of particles by the H9C2 cells, so the targeting effect is only twice that of the RBCM group. For the PCM/KALA group, PCM can improve the affinity between the particles and the H9C2 cells, while KALA can rapidly mediate the phagocytosis of particles by the H9C2 cells, so the targeting effect is 10 times that of the RBCM group. KALA plays a key role in mediating the rapid phagocytosis of particles by the H9C2 cells, but the targeting effect of PCM is the prerequisite. The results of antagonistic experiments show that if the H9C2 cells are pretreated with freePCM/KALA (PCM/KALA antagonistic group) so that the PCM receptor on the surface of H9C2 cells is blocked in advance, the cells can no longer effectively phagocytize particles of the PCM/KALA group, and has a targeting effect about twice that of the RBCM group. Similarly, the PCM antagonistic group pretreated with freePCM can also significantly reduce the phagocytosis of particles by the H9C2 cells. In conclusion, DNA&Pro@RBCM-PCM/KALA firstly binds to the surface of H9C2 cells through PCM in a targeting manner, and then achieves rapid cell phagocytosis with KALA.

Example 7

Lysosomal Escape Function of Biomimetic Nano-Protectant DNA&Pro@RBCM-PCM/KALA

Based on the above method, DNA&Pro@RBCM, DNA&Pro@RBCM-PCM and DNA&Pro@RBCM-PCM/KALA with FAM fluorescence label were prepared respectively for later use. H9C2 myocardial cells were spread in a confocal cell culture dish; nanoparticles in 3 experimental groups were added respectively when the confluence rate reached 70-80%; free particles were removed after 2 h; and the mixture was washed with PBS for 3 times. Subsequently, a fresh complete medium was added again; and lysosomal dye was added after continuous culture for 24 h. The mixture was incubated at 37° C. for 60 min, and then washed with PBS for 3 times; and DAPI dye was added to mark the nucleus. Finally, the co-location of particle fluorescence signal (green) and lysosomal fluorescence signal (red) in different experimental groups was observed by a CLSM imaging technology of a confocal laser scanning microscope. The results show that the lysosomal fluorescence signal (red) and the particle fluorescence signal (green) in the DNA&Pro@RBCM-PCM/KALA group almost are not overlapped, which indicates that the particles had escaped from lysosomes. On the contrary, the lysosomal fluorescence signal (red) and the particle fluorescence signal (green) in the DNA&Pro@RBCM-PCM or DNA&Pro@RBCM group are mostly overlapped at the same time point, which indicates that the particles are still in lysosomes (see FIG. 10). The above results indicate that the modification of KALA polypeptide can effectively mediate the particles to penetrate through lysosome and then enter cytoplasm.

Example 8

Different doses of biomimetic nano-protectant DNA&Pro@RBCM-PCM/KALA were added into H9C2 myocardial cells for incubation for 4 h; then, IC50 (50% Inhibitory Concentration) dose of DOX was added; the survival rate of H9C2 myocardial cells was detected with a CCK-8 reagent after 24 h; and a DOX group alone (with a DNA concentration of 0) and a treatment-free NC group (Negative Control) were set as experimental control groups. The results show that the survival rate of H9C2 cells is reduced to about 50% in the DOX group alone. However, with the increasing in the dose of biomimetic nano-protectant PCM/KALA-RBCM@DNA&Pro, the survival rate of H9C2 cells is gradually increased until the cell viability was completely protected, which indicates that the biomimetic nano-protectant PCM/KALA-RBCM@DNA&Pro has a concentration-dependent DOX adsorption effect (see FIG. 11). To further describe the protection mechanism of the biomimetic nano-protectant PCM/KALA-RBCM@DNA&Pro, in the invention, a dose of the biomimetic nano-protectant PCM/KALA-RBCM@DNA&Pr (NPs) is determined for protecting the damage of the IC50 dose of DOX to the H9C2 myocardial cells, while three important apoptosis pathway signal molecules (including Bax, Bcl2 and Caspase-3) are selected for Western Blot (WB) test (see FIG. 12). The results show that the PCM/KALA-RBCM@DNA&Pro nanoparticles significantly improve the expression of anti-apoptosis molecule Bcl2 and reduce the expression of pro-apoptosis molecule Bax after protection. In parallel, the cell viability experiment (FIG. 13) and the WB test (FIG. 14) prove that the biomimetic nano-protectant PCM/KALA-RBCM@DNA&Pro (NPs) can also protect QSG-7702 hepatocytes from damage caused by DOX.

Example 9

Figure 15A:
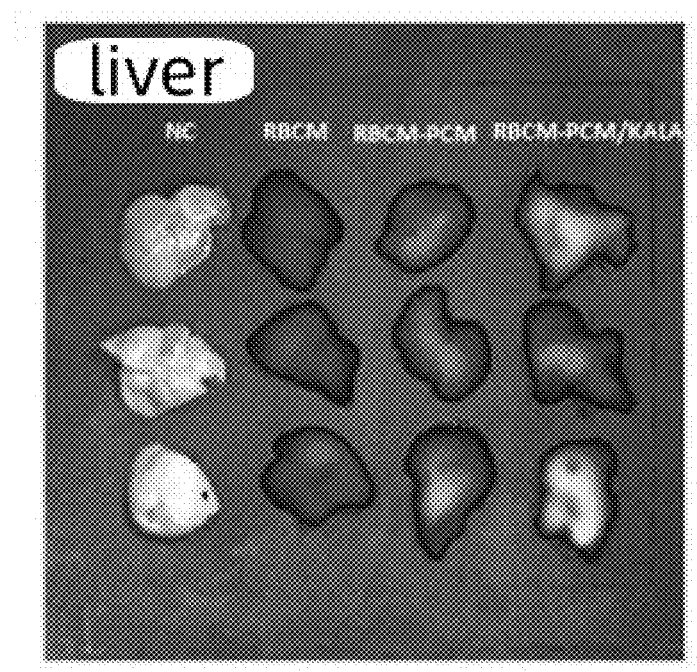
FIGS. 15A-15D show a schematic diagram of biodistribution of nanoparticles in different experimental groups in bodies of tumor-bearing B6 rats.
Figure 15A:
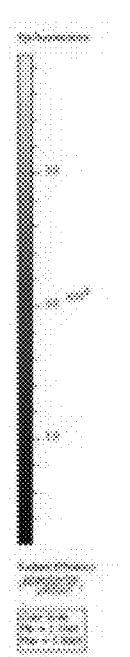
Figure 15B:
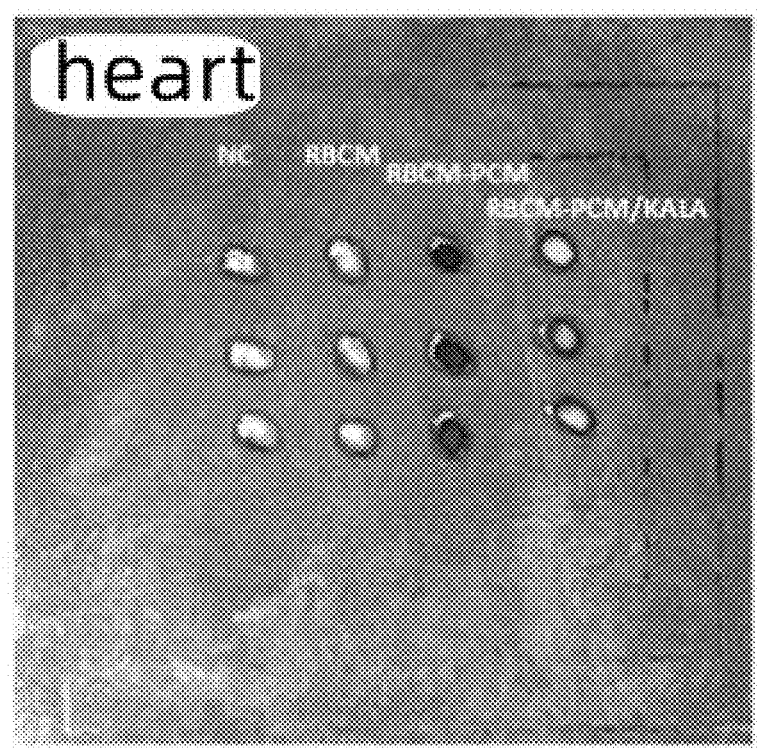
Figure 15B:
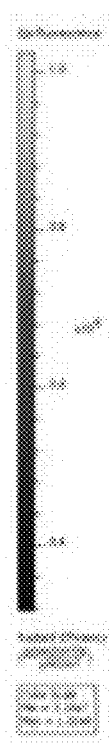
Figure 15C:
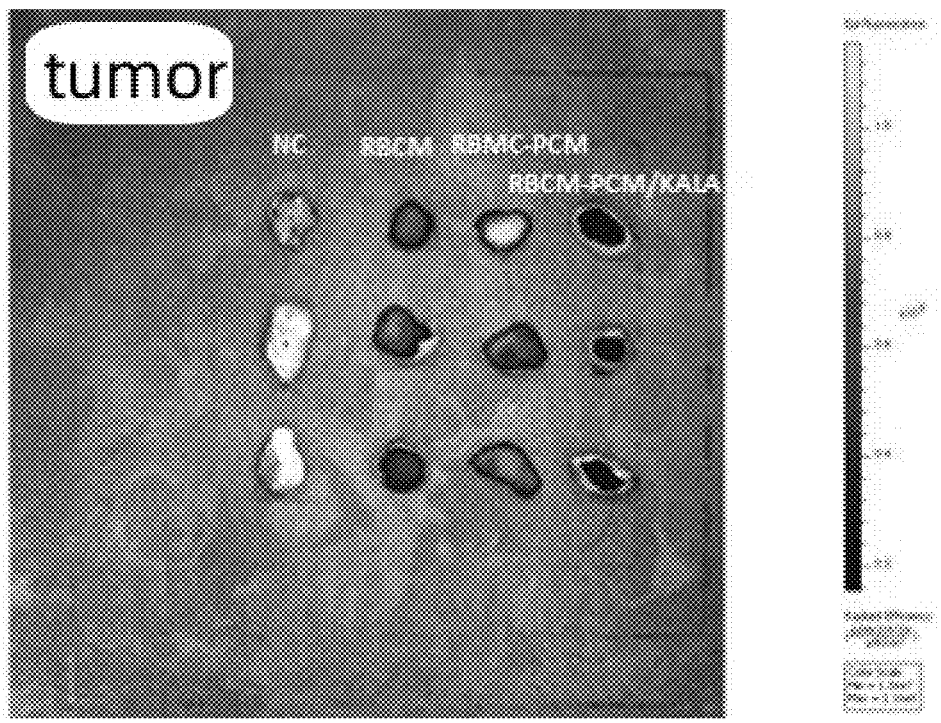
Figure 15D:
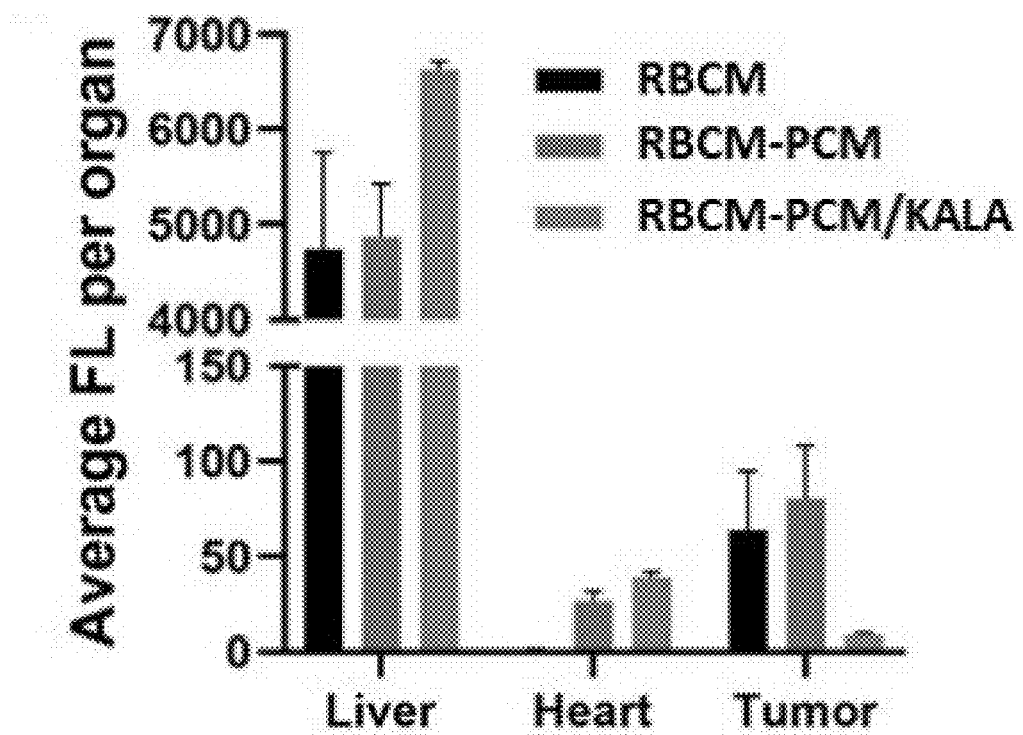
Figure 16:
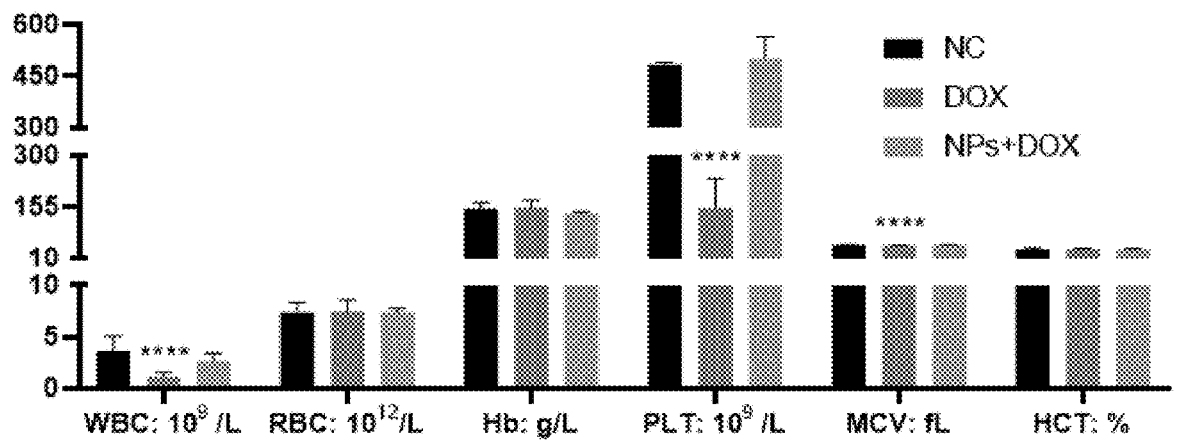
FIG. 16 is a schematic diagram of effect of a high dose of DOX (20 mg/kg) protected by the biomimetic nano-protectant DNA&Pro@RBCM-PCM/KALA on blood routine at a time point of Day8.
Figure 17:
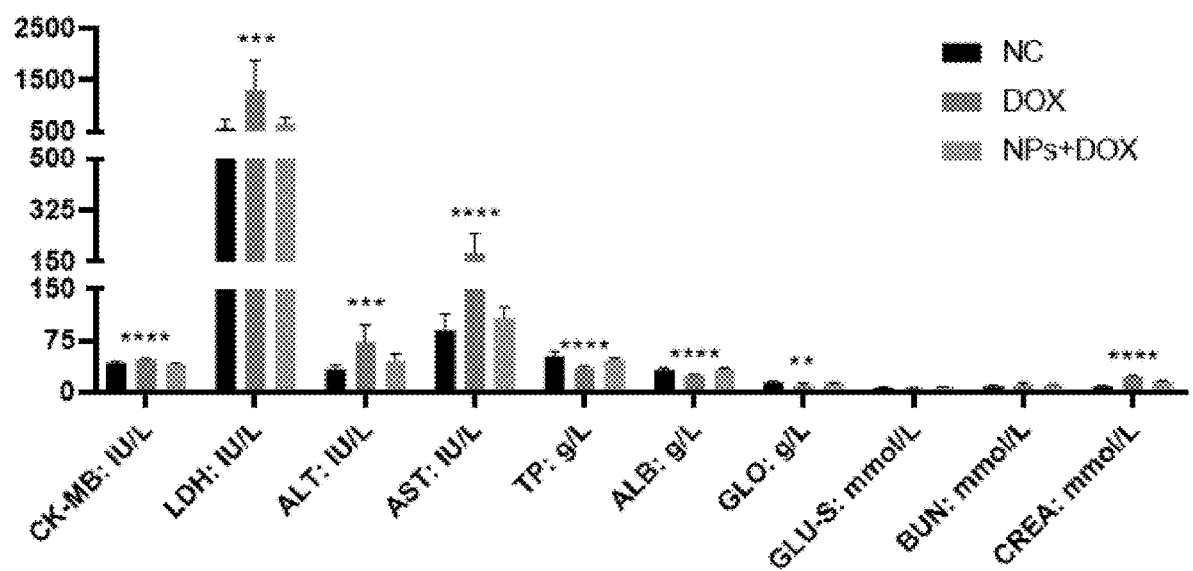
FIG. 17 is a schematic diagram of effect of the high dose of DOX (20 mg/kg) protected by the biomimetic nano-protectant DNA&Pro@RBCM-PCM/KALA on blood biochemistry at the time point of Day8.
Figure 18:
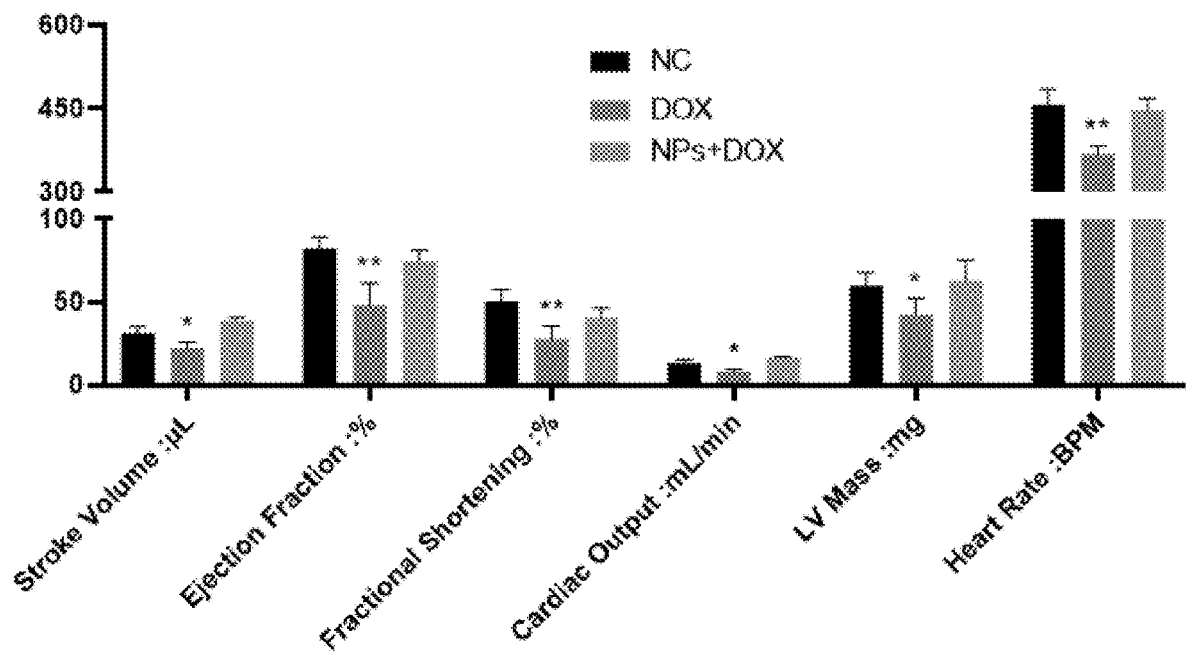
FIG. 18 is a schematic diagram of effect of the high dose of DOX (20 mg/kg) protected by the biomimetic nano-protectant DNA&Pro@RBCM-PCM/KALA on cardiac ultra-long axis at the time point of Day8.
Figure 19:
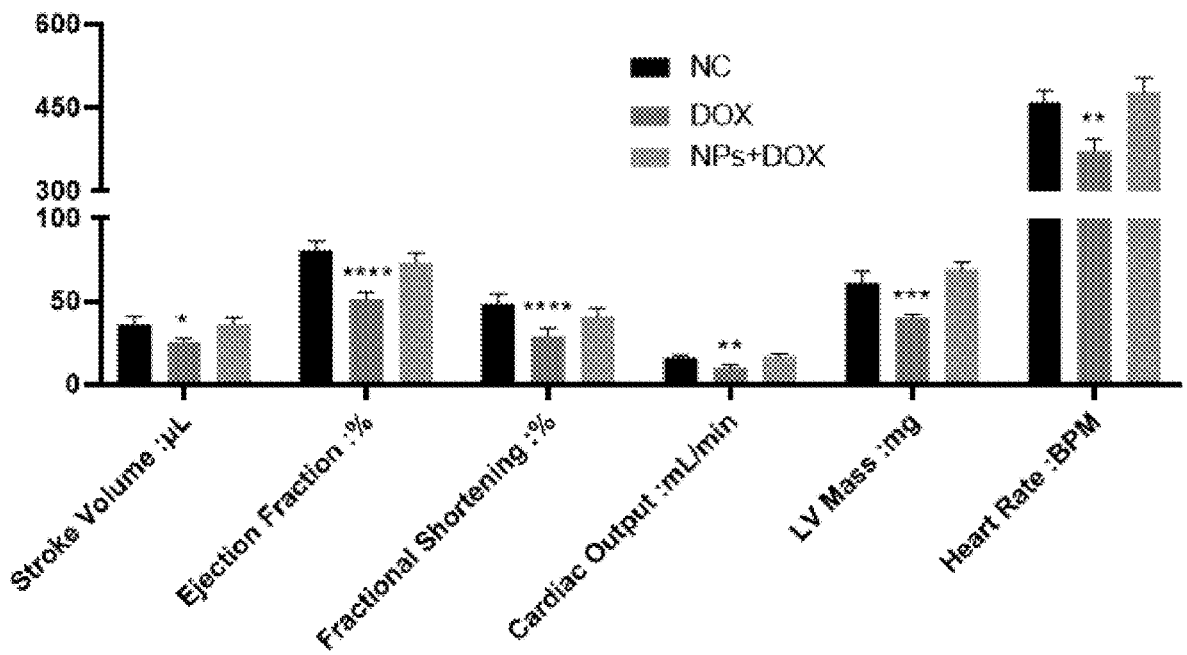
FIG. 19 is a schematic diagram of effect of the high dose of DOX (20 mg/kg) protected by the biomimetic nano-protectant DNA&Pro@RBCM-PCM/KALA on cardiac short axis at the time point of Day8.

Biodistribution of Biomimetic Nano-protectant PCM/KALA-RBCM@DNA&Pro in Tumor-bearing B6 Rats Backs of C57BL/6 rats (B6 rats) 6-8 weeks old were subcutaneously injected with $1\times10^6$ TC1 rat-derived cervical cancer cells to construct a subcutaneous transplanted tumor model of cervical cancer. DNA&Pro@RBCM-PCM/KALA (RBCM-PCM/KALA for short), DNA&Pro@RBCM-PCM (RBCM-PCM for short) and DNA&Pro@RBCM (RBCM for short) with DiD fluorescence label in RBCM membrane were respectively prepared according to the above method. When the tumor volume reached 200-300 mm³, three kinds of particles were injected into the bodies of B6 rats by caudal vein at a dose of RBCM membrane protein of 50 mg/kg (with a DNA dose of about 13 mg/kg); the B6 rats were dissected at a time point of 24 h; and the enrichment of nanoparticles in heart, liver and tumor tissues of the B6 rats in different experimental groups was detected by a small animal in-vivo imager (see FIGS. 15A-15D). The imaging results show that the enrichment of nanoparticles in the heart and liver is in an order of RBCM-PCM/KALA group>RBCM-PCM group>RBCM group (FIGS. 15A-B). On the contrary, the enrichment of nanoparticles at the tumor site in the RBCM-PCM/KALA group is much less than that in the other two groups, which indicates that the nanoparticles hardly or rarely enter the tumor site (FIG. 15C). On this basis, the heart, liver and tumor tissues of different experimental groups are homogenized; and the DiD fluorescence signal is quantitatively analyzed with an ELISA microplate reader (FIG. 15D). The results show that the total amount of fluorescence in homogenate of different tissues in different experimental groups is consistent with that in in-vivo imaging of small animals, which indicates that the biomimetic nano-protectant RBCM-PCM/KALA is effectively enriched in heart and liver, but does not enter the tumor tissues.

Example 10

Heart and Systemic Toxicity Caused by High Dose of DOX Protected with Biomimetic Nano-Protectant DNA&Pro@RBCM-PCM/KALA During Treatment of Tumor-bearing C57BL/6 Rats Backs of C57BL/6 rats (B6 rats) 6-8 weeks old were subcutaneously injected with $1\times10^6$ TC1 cells to construct a subcutaneous transplanted tumor model of cervical cancer. When the tumor volume reached 70-80 $mm^3$, a certain dose of biomimetic nano-protectant DNA&Pro@RBCM-PCM/KALA (80 mg/kg DNA, corresponding to the concentration of RBCM membrane protein of 300 mg/kg) was injected into bodies of B6 rats by caudal vein; and 20 mg/kg of DOX was injected after 24 h (DAY0, NPs+DOX group for short). Meanwhile, a DOX group alone and a treatment-free group (NC group) were set as experimental control groups. Subsequently, the weight and the tumor volume of B6 rats were observed every two days. By Day8, a protective effect of the biomimetic nano-protectant DNA&Pro@RBCM-PCM/KALA against cardiac and systemic toxicity from DOX was studied by blood routine, blood biochemical indexes and UCG indexes. The results show that at the time point of Day8 after injection with DOX, the NPs+DOX group can effectively alleviate or exempt the toxicity of DOX on blood routine, blood biochemistry and heart of B6 rats, and has various indexes without significant difference compared with the NC group. On the contrary, the DOX group has serious toxicity to blood routine, blood biochemistry and basic heart function of B6 rats (FIGS. 16-19). The information of relevant indexes is as follows: the blood routine indexes include white blood cells (WBC: $10^9$/L), red blood cells (RBC: $10^{12}$/L), hemoglobin (Hb: g/L), blood platelets (PLT: $10^9$/L), red blood cell volume (MCV: fL) and hematocrit (HCT: %); the blood biochemical indexes include serum creatine kinase isoenzyme (CKMB: IU/L), alanine aminotransferase (ALT: IU/L), aspartate aminotransferase (AST: IU/L), total protein (TP: g/L), albumin (ALB: g/L), globulin (GLO: g/L), blood glucose (GLU-S: mmol/L), blood urea nitrogen (BUN: mmol/L), creatinine (CREA: mmol/L) and lactate dehydrogenase (LDH: IU/L); and the UCG indexes include stroke volume per minute (SV, Stroke Volume: μL), ejection fraction (EF, Ejection Fraction: %), left ventricular shortening fraction (FS, Fractional Shortening: %), cardiac output (CO, Cardiac Output: mL/min), left ventricular mass (LV Mass, LV Mass: mg) and heart rate (HR, Heart Rate: Beat Per Minute, BPM).

Figure 20A:
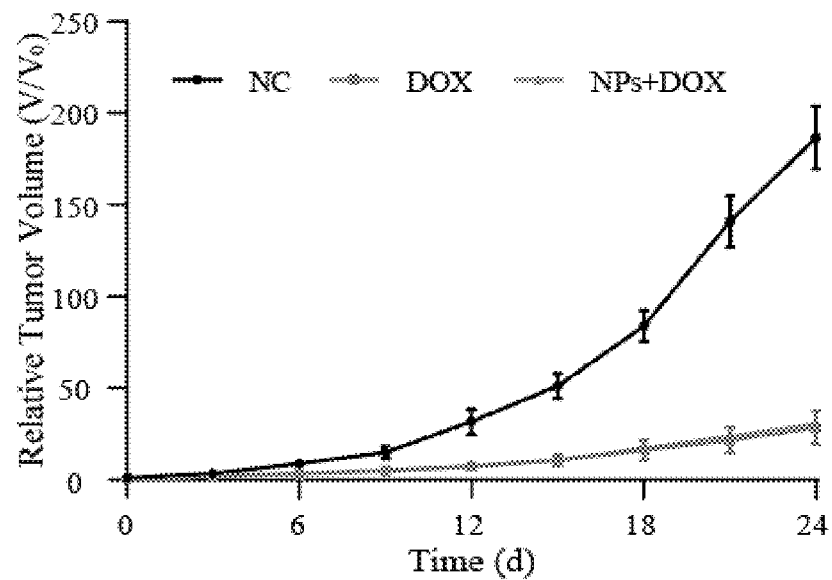
FIGS. 20A-20C show a schematic diagram of the biomimetic nano-protectant DNA&Pro@RBCM-PCM/KALA protecting the weight of tumor-bearing B6 rats without affecting the anti-tumor effect of DOX.
Figure 20B:
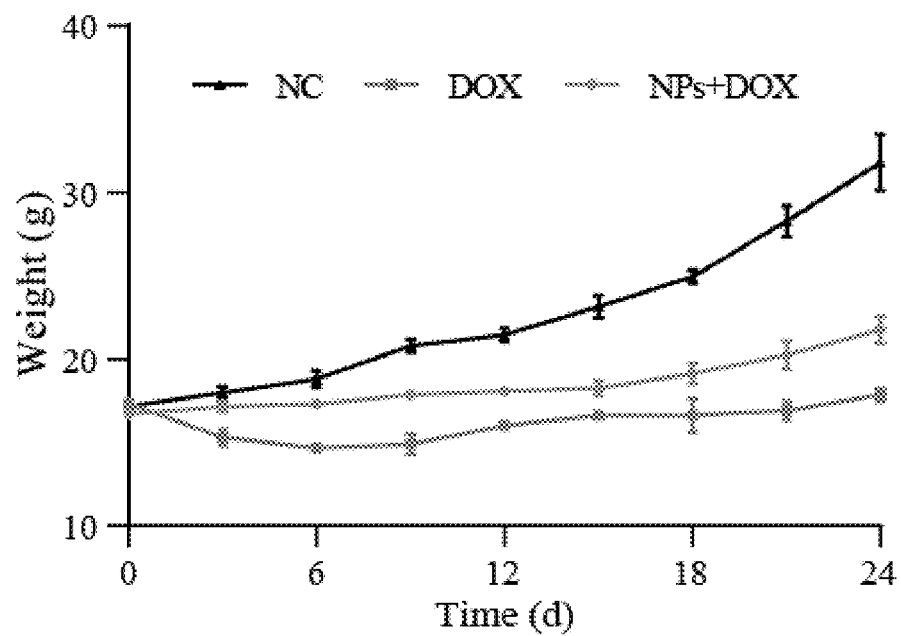
Figure 20C:
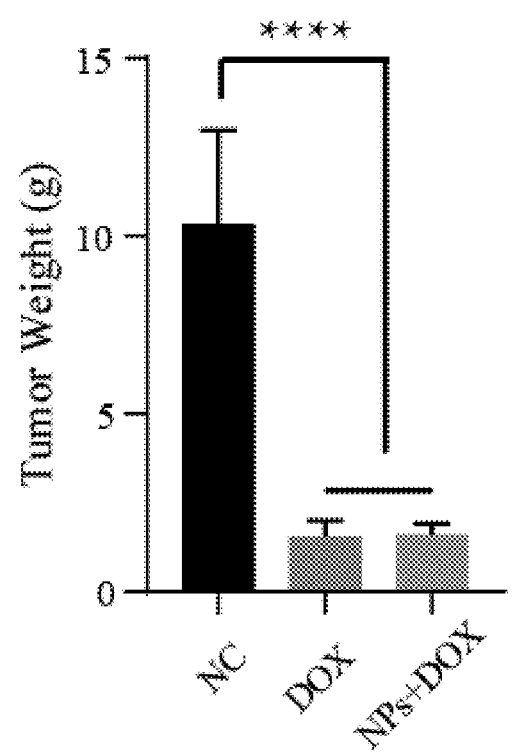

In parallel, backs of the B6 rats, 6-8 weeks old, were subcutaneously injected with $1\times10^6$ TC1 cells to construct a subcutaneous transplanted tumor model of cervical cancer. When the tumor volume reached 70-80 $mm^3$, the NPs+DOX group, the DOX group alone and the NC group were performed respectively; and then changes in size of tumor tissues and the changes in weight of B6 rats were observed and measured from Day0 to Day24. The results show that in the aspect of tumor inhibition effect, the growth trend of tumor tissues in the DOX group and the NPs+DOX group is apparently inhibited, and the volume at the end of Day24 is only about 15 times of the initial volume. However, the volume of tumor tissues in the NC group increases to about 200 times of the initial volume on Day24 (FIG. 20A). In the aspect of change in weight of B6 rats, the DOX group inhibits the tumor growth and causes serious cardiac and systemic toxicity, which is manifested as a sudden loss of weight. However, in the NPs+DOX group, NPs are distributed in normal organs such as heart and liver in advance, to effectively protect the normal organs from DOX damage, which is manifested as a steady increase of weight. Meanwhile, due to the rapid growth of tumor tissues in the NC group, the weight of NC group is increased greatly (FIG. 20B). In the process, the weight of B6 rats in the NPs+DOX group is significantly different from that in the NC group, but the weight data of tumor tissues in vitro are analyzed to show that the weight difference between the NC group and the NPs+DOX group is basically caused by the tumor weight (FIG. 20C). Therefore, under the protection of biomimetic nano-protectant DNA&Pro@RBCM-PCM/KALA (NPs), the weight of B6 rats does not reduce, but increases steadily, which indicates that the pretreatment with NPs can effectively protect the important organs such as heart and liver from damage without affecting the inhibition effect of DOX on the tumor tissues, which further confirms that NPs is only distributed in normal organs rather than tumor tissues.

CONCLUSION

In view of the high affinity of DOX to nuclear chromatin DNA, the invention relates to the preparation of a biomimetic nano-protectant with a nanoscale and a "chromatin-like" structure, which is used for protecting the DOX-induced cardiac and systemic toxicity. The biomimetic nano-protectant is composed of a cell membrane derived from organisms for modifying a myocardial cell targeting group, and a "chromatin-like" structure formed by the self-assembly of Pro and DNA fragments rich in GC base pairs. The protectant is swallowed by normal cells such as myocardial cells and then dispersed in cytoplasm, thereby effectively preventing DOX from entering the cell nucleus and preventing or alleviating cell apoptosis.

The myocardial cell targeting group is a fusion peptide PCM/KALA, with a sequence of (WSGTGRLARVTVVP-GAESLW(SEQ ID NO: 4 in C-terminus to N-terminus orientation)-CO-hydrazine hydrate-boc-WEAKLAKA-LAKALA-K(DDE)-HLAKALAKALKACEA (SEQ ID NO: 5)). The polypeptide PCM (with a sequence of WLSEAGPVVTVRALRGTGSW, as shown in SEQ ID NO: 4) has good affinity with myocardial cells and has a function of targeting myocardial cells; and the polypeptide KALA (with a sequence of WEAKLAKALAKALA-K(DDE)-HLAKALAKALKACEA, as shown in SEQ ID NO: 5) can mediate rapid phagocytosis of cells and subsequent lysosomal escape. Therefore, the fusion peptide PCM/KALA not only targets the myocardial cells and mediates the rapid phagocytosis of myocardial cells, but also can realize lysosomal escape in time, and can rapidly release the protectant as a barrier into the cytoplasm to build a barrier for the cell nucleus, to prevent DOX from damaging the cell nucleus, thereby preventing myocardial and/or liver cells from damage.

The specific action process is as follows: firstly, DNA&Pro@RBCM-PCM/KALA is integrally bound into the myocardial and/or liver cells in a targeting manner by the targeting effect of PCM; the polypeptide KALA maintains a secondary structure in an environment of pH=7.4; KALA also contains curled hydrophobic amino acids and exposed amino acids, wherein the exposed amino acids can mediate the rapid phagocytosis of KALA by cells; after KALA enters lysosomes, with the decrease of pH, the secondary structure of the polypeptide KALA is destroyed; the hydrophobic amino acids of KALA are exposed and fused with lysosomal membrane; and the escape of KALA polypeptide from lysosomes is mediated at this moment. Therefore, KALA can mediate the rapid phagocytosis of cells and the subsequent escape of lysosomes, thereby allowing DNA&Pro to be released into cells rapidly and building a protective barrier for the cell nucleus.

In the invention, the polypeptide PCM/KALA is coupled to the surface of RBCM to construct RBCM-PCM/KALA; then, DNA-Pro nanoparticles formed by the self-assembly of DNA and Pro are wrapped by the Extrusion method; and finally, a biomimetic nano-protectant DNA&Pro@RBCM-PCM/KALA of about 400 nm is constructed. DNA&Pro@RBCM-PCM/KALA can efficiently adsorb DOX and reduce the damage of DOX to normal cells. The biomimetic nano-protectant DNA&Pro@RBCM-PCM/KALA is only enriched in normal organs such as heart and liver, and rarely enters the tumor tissues, thereby protecting normal organs from damage of DOX (cardiac toxicity and the like) without affecting the tumor cell killing effect of DOX.

The above are only the preferred embodiments of the invention; a protection scope of the invention is not limited to the above embodiments; and all technical solutions under the concept of the invention should fall within the protection scope of the invention. It should be pointed out that for those ordinary skilled in the art, a number of improvements and retouching without departing from principles of the invention should also fall within the protection scope of the invention.

What is claimed is:

1. A preparation method of a biomimetic nano-protectant for detoxifying doxorubicin (DOX)-induced cardiac and systemic toxicity, comprising the following steps:
   obtaining and mixing the DNA sequence set forth in SEQ ID NO: 3 and protamine (Pro) to prepare DNA&Pro nanoparticles;
   reacting 1,2-distearoyl-sn-glycero-3-phosphoethanolamine-N-[maleimide(polyethylene glycol)-2000] (DSPE-PEG2000-MAL) with a fusion peptide PCM/KALA to prepare DSPE-PEG2000-PCM/KALA, wherein PCM is the peptide set forth in SEQ ID NO: 4 in C-terminus to N-terminus orientation and KALA is the peptide set forth in SEQ ID NO: 5;
   inserting DSPE-PEG2000-PCM/KALA into a surface of Red Blood Cell Membrane (RBCM) to prepare PCM/KALA-RBCM; and
   mixing the RBCM-PCM/KALA with the DNA&Pro nanoparticles to prepare a biomimetic nano-protectant DNA&Pro@RBCM-PCM/KALA.

2. The preparation method of the biomimetic nano-protectant according to claim 1, wherein the biomimetic nano-protectant DNA&Pro@RBCM-PCM/KALA is prepared by an Extrusion method after RBCM-PCM/KALA is mixed with the DNA&Pro nanoparticles.

3. The preparation method of the biomimetic nano-protectant according to claim 1, wherein a ratio of various components satisfies that DNA:protamine:RBCM:DSPE-PEG2000-MAL: PCM/KALA=6:5:150:3.75:7.5 (w/w).

4. The preparation method of the biomimetic nano-protectant according to claim 1, wherein the DNA sequence set forth in SEQ ID NO: 3 takes green fluorescent protein particles as a DNA template, with a size of 630 bp and a GC content of 65%.

5. The preparation method of the biomimetic nano-protectant according to claim 1, wherein DNA and Pro are mixed to form the DNA&Pro nanoparticles by an ultrasonic treatment for 20 s.

6. The preparation method of the biomimetic nano-protectant according to claim 5, wherein a nitrogen-phosphorus ratio of a mixture of DNA and Pro satisfies N/P=2.

7. The preparation method of the biomimetic nano-protectant according to claim 1, wherein a ratio of the DSPE-PEG2000-MAL to PCM/KALA is 1:2 (mol/mol); and DSPE-PEG2000-MAL and PCM/KALA are dissolved in ultra-pure water, and incubated at 37° C. for 30-60 min to synthesize DSPE-PEG2000-PCM/KALA.

8. The preparation method of the biomimetic nano-protectant according to claim 1, wherein DSPE-PEG2000-PCM/KALA and RBCM are mixed at a mass ratio of 1:20 (w/w) by membrane protein mass, and incubated at 37° C. for 30-60 min to prepare RBCM-PCM/KALA.

9. The preparation method of the biomimetic nano-protectant according to claim 2, wherein DNA&Pro@RBCM-PCM/KALA is prepared by the Extrusion method, with a pore size of 400 nm.

* * * * *

SEQUENCE LISTING

```
<160> NUMBER OF SEQ ID NOS: 5

<210> SEQ ID NO 1
<211> LENGTH: 18
<212> TYPE: DNA
<213> ORGANISM: Artificial Sequence
<220> FEATURE:
<223> OTHER INFORMATION: The sequence is synthetized.

<400> SEQUENCE: 1
cggccacaag ttcgtgat                                                 18

<210> SEQ ID NO 2
<211> LENGTH: 22
<212> TYPE: DNA
<213> ORGANISM: Artificial Sequence
<220> FEATURE:
<223> OTHER INFORMATION: The sequence is synthetized.

<400> SEQUENCE: 2
aatccagagg ttgattgttc ca                                            22

<210> SEQ ID NO 3
<211> LENGTH: 657
<212> TYPE: DNA
<213> ORGANISM: Artificial Sequence
<220> FEATURE:
<223> OTHER INFORMATION: The sequence is synthetized.

<400> SEQUENCE: 3
cggccacaag ttcgtgatca ccggcgaggg catcggctac cccttcaagg gcaagcaggc    60
catcaacctg tgcgtggtgg agggcggccc cttgcccttc gccgaggaca tcttgtccgc   120
cgccttcatg tacggcaacc gcgtgttcac cgagtacccc caggacatcg tcgactactt   180
caagaactcc tgccccgccg gctacacctg ggaccgctcc ttcctgttcg aggacggcgc   240
cgtgtgcatc tgcaacgccg acatcaccgt gagcgtggag gagaactgca tgtaccacga   300
gtccaagttc tacggcgtga acttccccgc cgacggcccc gtgatgaaga agatgaccga   360
caactgggag ccctcctgcg agaagatcat ccccgtgccc aagcagggca tcttgaaggg   420
cgacgtgagc atgtacctgc tgctgaagga cggtggccgc ttgcgctgcc agttcgacac   480
cgtgtacaag gccaagtccg tgccccgcaa gatgcccgac tggcacttca tccagcacaa   540
```

-continued

```
gctgaccege gaggaccgca gcgacgccaa gaaccagaag tggcacctga ccgagcacgc    600
catcgcctcc ggctccgcct tgccctgaac gcgtctggaa caatcaacct ctggatt      657
```

<210> SEQ ID NO 4
<211> LENGTH: 20
<212> TYPE: PRT
<213> ORGANISM: Artificial Sequence
<220> FEATURE:
<223> OTHER INFORMATION: The sequence is synthetized.

<400> SEQUENCE: 4

Trp Leu Ser Glu Ala Gly Pro Val Val Thr Val Arg Ala Leu Arg Gly
1               5                   10                  15

Thr Gly Ser Trp
            20

<210> SEQ ID NO 5
<211> LENGTH: 30
<212> TYPE: PRT
<213> ORGANISM: Artificial Sequence
<220> FEATURE:
<223> OTHER INFORMATION: The sequence is synthetized.
<220> FEATURE:
<221> NAME/KEY: MISC_FEATURE
<222> LOCATION: (15)..(15)
<223> OTHER INFORMATION: lysine modified with DDE protecting group

<400> SEQUENCE: 5

Trp Glu Ala Lys Leu Ala Lys Ala Leu Ala Lys Ala Leu Ala Lys His
1               5                   10                  15

Leu Ala Lys Ala Leu Ala Lys Ala Leu Lys Ala Cys Glu Ala
            20                  25                  30